(12) United States Patent
Kornilovich

(10) Patent No.: US 7,406,222 B2
(45) Date of Patent: Jul. 29, 2008

(54) COMPOSITE EVANESCENT WAVEGUIDES AND ASSOCIATED METHODS

(76) Inventor: Pavel Kornilovich, 1000 NE. Circle Blvd., Corvallis, OR (US) 97330-4239

( * ) Notice: Subject to any disclaimer, the term of this patent is extended or adjusted under 35 U.S.C. 154(b) by 53 days.

(21) Appl. No.: 11/357,587

(22) Filed: Feb. 16, 2006

(65) Prior Publication Data

US 2007/0189666 A1    Aug. 16, 2007

(51) Int. Cl.
*G02B 6/26* (2006.01)
(52) U.S. Cl. ............... 385/30; 385/27; 385/37; 385/129; 385/130
(58) Field of Classification Search ........ 385/129, 385/130, 30, 27, 14, 37
See application file for complete search history.

(56) References Cited

U.S. PATENT DOCUMENTS

| | | | |
|---|---|---|---|
| 5,327,225 A * | 7/1994 | Bender et al. ............ 356/445 |
| 5,633,561 A | 5/1997 | Barker |
| 5,973,316 A * | 10/1999 | Ebbesen et al. ........... 250/216 |
| 6,340,448 B1 | 1/2002 | Naya et al. |
| 6,438,149 B1 | 8/2002 | Taychati et al. |
| 6,579,721 B1 * | 6/2003 | Natan et al. ............... 436/164 |
| 6,643,439 B2 | 11/2003 | Notomi et al. |
| 6,694,067 B1 | 2/2004 | O'Keefe et al. |
| 6,780,499 B2 | 8/2004 | Gates et al. |
| 7,194,164 B2 * | 3/2007 | Iazikov et al. ............ 385/37 |
| 2003/0021578 A1 * | 1/2003 | Zhong et al. ............. 385/144 |
| 2003/0141507 A1 * | 7/2003 | Krames et al. ............ 257/79 |
| 2004/0005133 A1 * | 1/2004 | Johannessen ............. 385/130 |
| 2005/0089287 A1 | 4/2005 | Eggleton et al. |
| 2005/0213310 A1 | 9/2005 | Takeda |
| 2007/0017797 A1 * | 1/2007 | Hyde ...................... 204/157.15 |
| 2007/0018077 A1 * | 1/2007 | Puscasu et al. ........... 250/210 |
| 2007/0020157 A1 * | 1/2007 | Hyde ...................... 422/186 |
| 2007/0034978 A1 * | 2/2007 | Pralle et al. .............. 257/432 |
| 2007/0189666 A1 * | 8/2007 | Kornilovich ............. 385/30 |

FOREIGN PATENT DOCUMENTS

| WO | WO 2004/095084 | 11/2004 |
|---|---|---|
| WO | WO 2005/062347 | 7/2005 |

OTHER PUBLICATIONS

Simin Feng, et al., Optical properties of multilayer metal-dielectric nanofilms with all evanescent modes, Optics Express, May 30, 2005, pp. 4113-4124, vol. 13, No. 11.

Phillippe Lalanne, Mike Hutley, The optical properties of artificial media structured at a subwavelength scale, web site gea.df.uba.ar/curso2002/lect3.pdf, accessed Dec. 12, 2005.

(Continued)

*Primary Examiner*—Frank G Font
*Assistant Examiner*—James P. Hughes

(57) ABSTRACT

A composite evanescent waveguide can include a first structured dielectric layer and a second dielectric material oriented adjacent one another to form a wave propagation interface between the first structured dielectric layer and second dielectric material. Each of the first structured dielectric layer and second dielectric material are formed of materials such that the wave propagation interface can be capable of propagating an all-evanescent surface wave. The resulting propagating surface waves tend to have low losses and can be suitable for optical communications, surface analysis, sensors, and a variety of other applications.

27 Claims, 3 Drawing Sheets

OTHER PUBLICATIONS

John B. Pendry and David R. Smith, Reversing Light With Negative Refraction, Physics Today on-line, Dec. 2003, pp. 1-18.

Carsten Marquart, et al., Near-field imaging of surface plasmon-polariton guiding in band gap structures at telecom wavelengths, Optics Express, May 2, 2005, pp. 3303-3309, vol. 13, No. 9.

R. Quidant, et al, Frustrated energy transport through microwaveguides decorated by gold nanoparticle chains, Europhysics Letters, Jun. 15, 2004, pp. 785-791.

Surface Plasmon Resonance—a method to analyze interfacial optical properties and to develop biosensors, chem..ch.huji.ac.il/~eugeniik/spr.htm, accessed Oct. 26, 2005, pp. 1-11.

Bernard Schneider, Battling Bio-Terrorism, Spie's Magazine, Special focus section, Apr. 2002, pp. 21-23.

Aristeidis Karalis, et al. Surface-Plasmon-Assisted Guiding of Broadband Slow and Subwavelength Light in Air, Physical Review Letters, The American Physical Society 2005, Aug. 5, 2005, pp. 063901-1-063901-4.

C. David, et al. Nano-structured anti-reflective surfaces replicated by hot embossing, Microelectronic Engineering 61-62 (2002) 435-440, www.elsevier.com/locate/mee.

Carsten Henkel and Vahid Sandoghdar, Single-molecule spectroscopy near structured dielectrics, Optics Communications, Oct. 6, 1998.

Surface Plasmon Resonance, SPR Pages—Surface Plasmon Resonancec, accessed Oct. 25, 2005, pp. 1-7, http://home.hccnet.nl/ja.marquart/BasicSPR/BasicSpr01.htm.

* cited by examiner

COMPOSITE EVANESCENT WAVEGUIDES AND ASSOCIATED METHODS

BACKGROUND OF THE INVENTION

On-chip optical communications and optical interconnects are the subject of substantial research and interest in the field of micro- and nano-photonics. Many in the industry anticipate light replacing electrons as global interconnects on high-performance chips. However, photonic waveguides generally require very high precision in order to reduce scattering losses and can be difficult to fabricate.

FIG. 1 illustrates a cross-sectional view of a typical photonic crystal slab waveguide. In such devices, a slab of silicon 10 can be perforated with holes 12 across selected areas of the slab to form a guiding layer 14. Certain areas of the silicon slab can be left intact with no perforations. The slab thickness is generally chosen close to half the wavelength of propagating light in the guiding layer such that the waveguide is single mode. The propagating mode 16 exhibits a typical Gaussian wave form where the field evanesces outside of the guiding layer and has a Gaussian bell curve shape within the guiding layer. These devices also require a low refractive index substrate 18 between the guiding layer and the underlying substrate 20. Typically, these low refractive index substrates can be difficult and expensive to manufacture, especially those with refractive index approaching one. Substrates having higher refractive indices allow the propagating mode to leak into the substrate increasing loss. A number of efforts have focused on improving the quality and properties of these low index substrates with moderate to limited success. As such, photonic waveguide devices with reduced losses and increased ease of manufacture continue to be sought.

BRIEF DESCRIPTION OF THE DRAWINGS

Several aspects of the invention can be better understood with reference to the following drawings. The components in the drawings are not necessarily to scale, with emphasis instead being placed upon clearly illustrating the principles of the present invention.

DETAILED DESCRIPTION OF THE INVENTION

Figure 1:
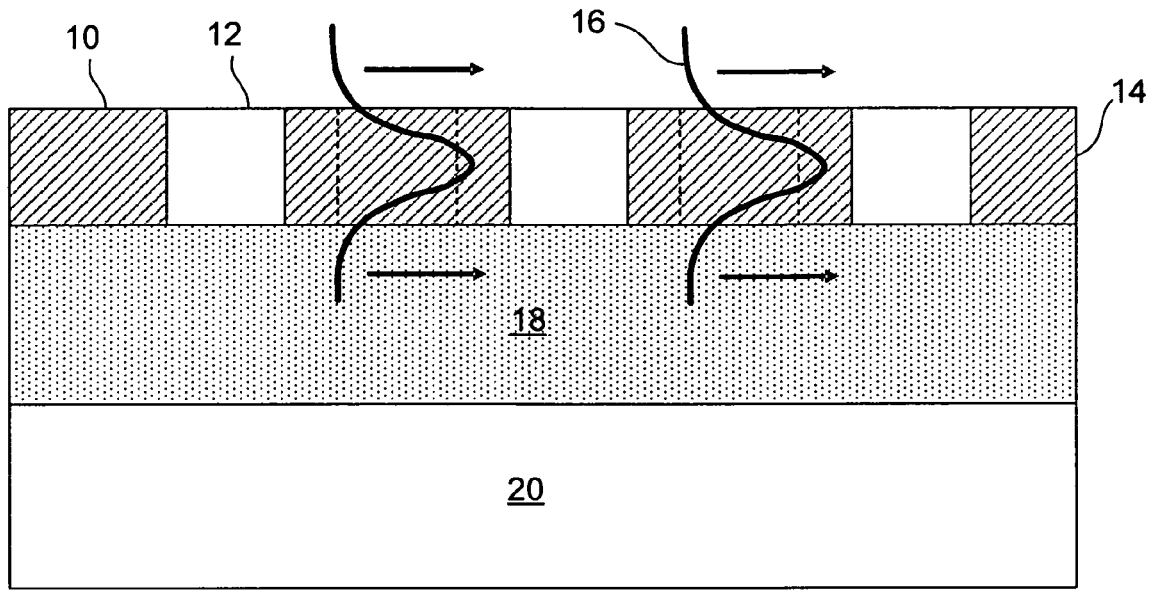
FIG. 1 illustrates a side cross-sectional view of a photonic crystal slab waveguide in accordance with the prior art.

Reference will now be made to exemplary embodiments and specific language will be used herein to describe the same. It will nevertheless be understood that no limitation of the scope of the invention is thereby intended. Alterations and further modifications of the inventive features described herein, and additional applications of the principles of the invention as described herein, which would occur to one skilled in the relevant art and having possession of this disclosure, are to be considered within the scope of the invention.

Further, before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used.

The singular forms "a," "an," and "the" include plural referents unless the context clearly dictates otherwise. Thus, for example, reference to "a waveguide" includes reference to one or more of such devices and reference to "a layer" includes reference to one or more of such layers.

As used herein, "waveguide" refers to any structure which acts to confine an electromagnetic wave along a designed path. Conventional waveguides include enclosed tunnel structures; however, waveguides of the present invention can also include structures which are multilayered, periodic in one, two or three dimensions, non-enclosed, or the like as shown in the accompanying figures.

As used herein, "structured dielectric" refers to a composite dielectric material which includes at least two different materials, at least one of which is a dielectric. Examples of dielectric materials can include, but are certainly not limited to, gases such as air, gas mixtures, fluids, including liquids such as water, fluid mixtures, and solids such as glass or silicon. Structured dielectrics can include photonic crystals, metamaterials, and the like. However, often a structured dielectric can be formed by a regular or irregular pattern of one dielectric material embedded inside a matrix of another dielectric material. For example, silicon dioxide can be imbedded in a silicon matrix, air embedded in glass matrix, and so on. However, in some cases a semi-conducting material can comprise either the matrix or the embedded regions while the other material can be a dielectric. The embedded regions can have the shape of rods, boxes, spheres, cylinders, and other geometrical forms. The embedded regions can form a connected network or can be spaced apart. Those skilled in the art continue to develop various structures and configurations for structured dielectrics, of which many would be suitable for use in the present invention so long as the parameters for the overall device claimed are satisfied.

As used herein, "uniform dielectric" refers to an object made of substantially homogeneous dielectric material. Non-limiting examples of common uniform dielectrics can include glass and air. Uniform dielectric can be regarded as an extreme case of a structured dielectric in the limit of vanishingly small embedded regions.

As used herein, "propagating" when referring to a wave refers to the ability of a bulk material, interface, or linear structure to predictably guide a wave along a path with acceptable losses and acceptable absorption. Acceptable losses and absorption allow for the device to be used for its intended and designed purpose. Although acceptable losses can vary somewhat depending on the particular device and required propagation distance, losses of less than about 10 dB/cm are generally considered acceptable.

Figure 2:
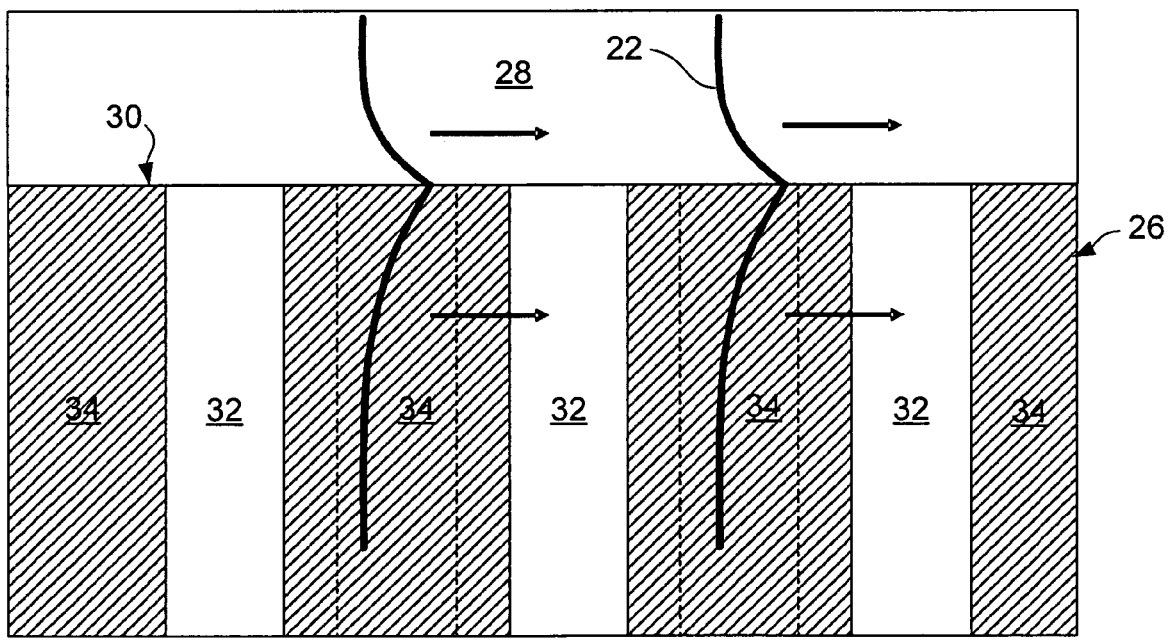
FIG. 2 illustrates a side cross-sectional view of a composite evanescent waveguide in accordance with one embodiment of the present invention.

As used herein, "all-evanescent" refers to a type of wave form wherein all modes and portions of the wave exhibit evanescence in all directions except the direction of propagation. An example of a typical all-evanescent wave 22 in accordance with the present invention is shown in FIG. 2.

As used herein, "surface wave" refers to a wave that is guided along the interface between two different media or by a refractive index gradient.

As used herein, "index guided" means that the effective index of the surface mode is larger than the effective index of the adjacent dielectric material, e.g. 1.0 for air, 1.5 for glass, etc. In this way, the surface mode is index guided on the side internal to the structured dielectric. An index guided mode is one where leaking and loss of energy is substantially prevented under the momentum and energy conservation laws.

As used herein, "total internal reflection" refers to when a first dielectric material has an effective refractive index less than the effective refractive index of a second adjacent dielectric material with respect to waves approaching the interface from the second material.

As used herein, "frequency" and "wavelength," the latter meaning "wavelength in free space," characterize the temporal and spatial periodicity of the electromagnetic wave. Since there is a one-to-one correspondence between the frequency and wavelength in free space (their product is equal to the speed of light in free space), they are used herein interchangeably to characterize a wave.

As used herein, "effective" when referring to optical properties of a material mean the overall or average property. For example, structured dielectrics typically have a periodic refractive index corresponding to each material based on the specific location. However, on average, a traveling wave experiences an overall response to the material which is a combined contribution from each material. Thus, the term "effective" refers to this combined contribution on various properties of the material.

As used herein, "effective index" is defined as the ratio of the speed of light in vacuum to the phase velocity of the surface mode. The phase velocity is defined as an inverse of the product of the wave frequency and the wavelength of the propagating surface mode in the material. The index of refraction or effective index of refraction, n, is a commonly measured and calculated property of particular materials.

As used herein, "light transmissive" is used to describe a material which allows light to transmit through the material at a particular wavelength or range of wavelengths. Light transmissive materials can be either translucent or transparent and can be visibly opaque or clear. For example, silicon is light transmissive at wavelengths of about 1.55 μm.

As used herein, "vapor deposition" refers to a process of depositing materials on a substrate through the vapor phase. Vapor deposition processes can include any process such as, but not limited to, chemical vapor deposition (CVD) and physical vapor deposition (PVD). A wide variety of each vapor deposition method can be performed by those skilled in the art. Examples of vapor deposition methods include hot filament CVD, rf-CVD, laser CVD (LCVD), metal-organic CVD (MOCVD), sputtering, thermal evaporation PVD, ionized metal PVD (IMPVD), electron beam PVD (EBPVD), reactive PVD, atomic layer deposition (ALD) and the like.

As used herein, "solution phase deposition" refers to a process of depositing materials on a substrate via a liquid phase. A number of solution phase deposition processes can be suitable. Non-limiting examples can include roll coating, gravure coating, spin coating, dip coating, spray coating, extrusion coating, and the like.

As used herein, "ink-jetting" refers to the well known process of depositing liquids using ink-jet architecture, and is in no way limited to depositing inks or ink-containing compositions, i.e., compositions containing a colorant. Common suitable ink-jet architectures include thermal ink-jet and piezoelectric ink-jet printheads. Further, ink-jetting of materials on a substrate can include direct contact of such material with the substrate or can indicate that the material is printed indirectly on the substrate by contact with a separate material or layer.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a range of about 1 to about 500 should be interpreted to include not only the explicitly recited limits of 1 and about 500, but also to include individual values such as 2, 3, 4, and sub-ranges such as about 10 to 50, about 20 to 100, etc.

It is to be understood that the various features shown in the attached figures are for the purposes of illustration and do not in any manner limit the present invention. In particular, structures or layers are represented in the figure by cross-hatch or dot markings. These markings are used to differentiate layers, and are not to be construed to limit the invention to any particular type of material, even in the case where the type of markings used may correspond to markings used by those in various fields of endeavor to indicate a type of material.

Referring now to FIG. 2, a composite evanescent waveguide in accordance with one embodiment of the present invention is shown generally. The composite evanescent waveguide can include a first structured dielectric layer 26 and a second dielectric material 28 oriented adjacent one another to form a wave propagation interface 30 between the first structured dielectric layer and second dielectric material. The first structured dielectric layer can have a first effective dielectric constant and can comprise a number of different materials as discussed in more detail below. Each of the first structured dielectric layer and second dielectric material can contribute to the properties at the wave propagation interface. In accordance with the present invention, the wave propagation interface can be capable of propagating an all-evanescent surface wave at one or more specific frequencies. Further, each of the structured dielectric layer and the dielectric material can be chosen and configured such that the propagating surface wave can be index guided.

The first structured dielectric layer 26 can be formed of any suitable dielectric materials. The structured dielectric can typically include a dielectric matrix having a plurality of second dielectric regions embedded therein in a regular pattern. However, irregularly spaced regions can also be suitable. Further, the specific dielectric materials which comprise the first structured dielectric layer are not particularly limited, except as otherwise noted herein. Non-limiting examples of dielectric materials suitable for use in the first structured dielectric layer can include silicon, glass, sapphire, diamond, quartz, magnesium fluoride, silicon oxide, germanium oxide, tantalum oxide, titanium oxide, transparent polymers, and combinations or composites thereof. In an additional aspect of the present invention, the structured dielectric can comprise a low electrical conductivity material such as, but not limited to, undoped and low-doped semiconductors (e.g. materials with an energy gap between about 0.25 eV and about 4 eV) such as silicon, and transparent conductive oxides at low doping or even without a dopant such as doped or undoped zinc tin oxide. Such low conductivity materials can be suitable for the present invention as long as their plasma frequency remains substantially smaller (e.g. generally at least 10 times smaller) than the frequency of the propagating mode such that the material remains transparent. In one specific embodiment, the first structured dielectric can comprise a dielectric matrix of silicon with air embedded regions. As a general matter, suitable dielectric transparent materials can have a refractive index from about 1.35 to about 2.5, and in some cases from about 1.0 (e.g. gases) to about 4.0 (e.g. undoped and low doped semiconductors).

Suitable structured dielectric layers can be formed in a wide variety of arrangements. For example, a plurality of cylindrical holes can be formed in the matrix. The holes can be filled with air or any other suitable dielectric material in order to achieve the desired wave guide properties discussed herein. In one aspect, the free space regions can have the form of substantially mutually parallel holes. In another aspect, a cross-section of the holes can be substantially circular. However, elliptical cross-sections can also be suitable.

Generally, the structured dielectric layer can be a two- or three-dimensional periodic structured dielectric. Two-dimensional structured dielectric materials can include embedded regions which exhibit changes in composition over two dimensions and a homogeneous and uniform composition in a third dimension substantially at an angle between 0 and 90 degrees to the direction of propagation of a wave. The uniformity in composition in the third dimension can extend a distance which is greater than the tail of the field into the material. For example, FIG. 2 illustrates a plurality of cylindrical holes 32 oriented substantially perpendicular to the propagation direction and extending into the matrix 34 for a sufficient depth such that the waves 22 do not encounter a boundary along the third dimension. Alternatively, the first structured dielectric layer can be a three-dimensional periodic structured dielectric. For example, spheres or small rods can be dispersed in a dielectric matrix. One specific example of a three-dimensional embedded material can include silicon dioxide beads.

Figure 3:
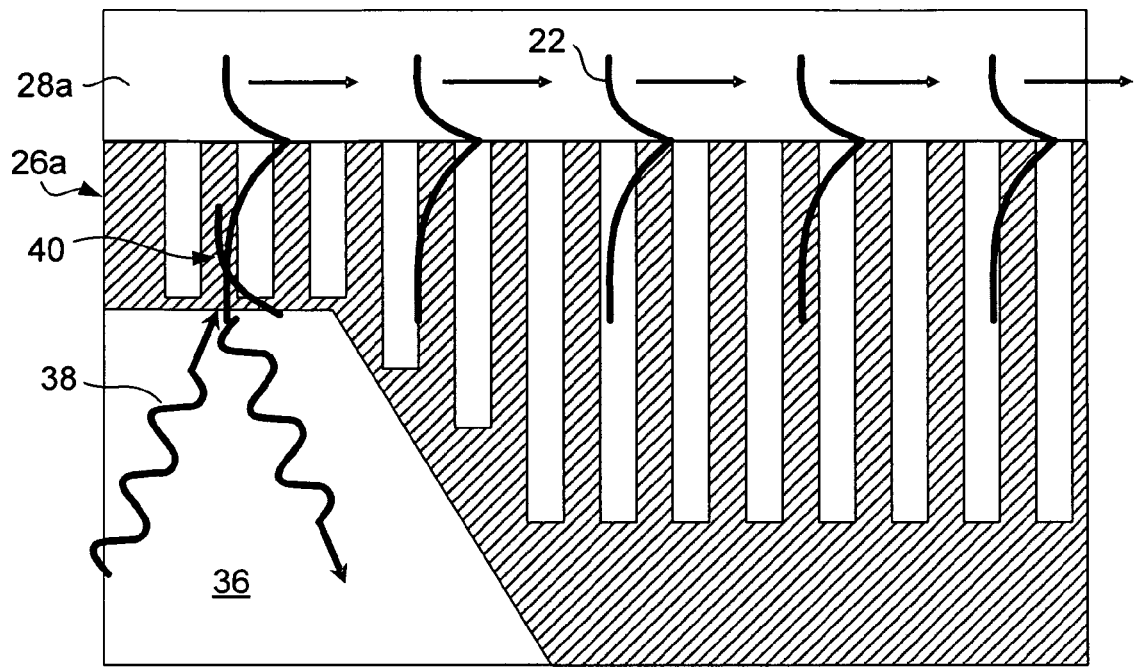
FIG. 3 illustrates a side cross-sectional view of a coupling in connection with another embodiment of the present invention.
Figure 4:
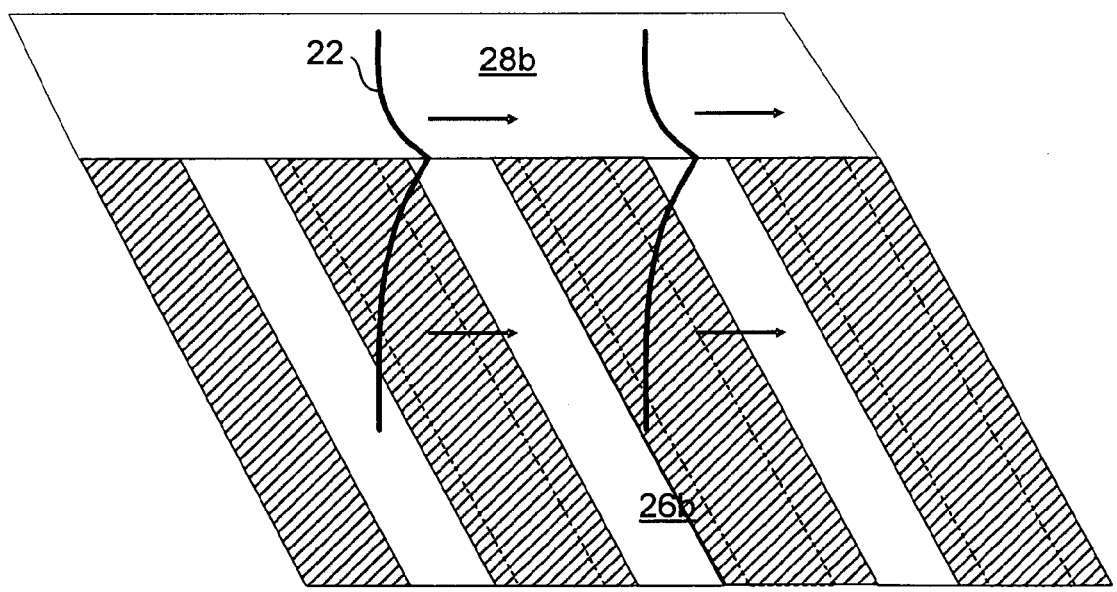
FIG. 4 illustrates a side cross-sectional view of a composite evanescent waveguide in accordance with another embodiment of the present invention.

In one alternative embodiment, the first structured dielectric layer can be a silicon matrix having a triangular lattice of cylindrical holes which are parallel. For a hole-to-hole distance of about 360 nm and hole diameters of about 220 nm, a wide photonic band gap exists for waves with wavelengths at about 1.55 μm propagating perpendicular to the axes of the cylindrical holes. It is noted that FIGS. 2 and 3 illustrate holes which are vertical and perpendicular to a plane of the second dielectric material 28. However, the holes or other embedded structures can be oriented in any manner to allow the resulting photonic band gap in the direction of propagation. For example, the cylinders can be oriented at an angle less than 90 degrees to the direction of propagation, as illustrated in FIG. 4. In FIG. 4, holes of the structured dielectric layer 26b can be angled as shown with a dielectric material 28b. Each of these materials can be formed as discussed herein with respect to the structures shown in FIG. 1 to obtain an all-evanescent wave 22. As another example, the cylinders can be perpendicular to the direction of propagation of the surface waves and parallel to the plane of the second dielectric material. These holes, as well as many other structured patterns, can be formed by any known process such as, but not limited to, anisotropic etching, focused ion-beam, self-assembly mechanisms, nanolithography, templating, and the like.

The physical dimensions of the structured dielectric layer can vary considerably depending on the designed frequency of operation and the intended application. However, as a general guideline the thickness of the first structured dielectric layer can range from about 0.5 μm to about 5 mm.

The second dielectric material can be formed of any suitable dielectric and can be a uniform dielectric or a structured dielectric. In some embodiments of the present invention, the second dielectric material can be a uniform dielectric. Several non-limiting examples of suitable uniform dielectrics can include air (n is about 1), glass (n is about 1.5), and magnesium fluoride (n is about 1.37). Depending on the application, the uniform dielectric can be air. Designing the composite waveguide of the present invention using air as the second dielectric material can decrease manufacture costs.

Alternatively, the second dielectric material can be a structured dielectric. Designing the composite waveguides of the present invention using a second structured dielectric can allow for increased flexibility in achieving propagation of all-evanescent modes at various frequencies. Similar to the discussion above for the first dielectric layer, the second dielectric material can be a two- or three-dimensional periodic structured dielectric and can utilize the same materials and configurations as discussed above. One example of an irregular periodic structured second dielectric is porous silica with variable degree of porosity and refractive index between about 1.1 and about 1.4.

Although the above discussion allows for relatively broad utilization of materials, geometries, and configurations, the devices of the present invention are specifically designed to allow for propagation of an all-evanescent surface wave at the wave propagation interface. The combination of materials, geometries, and configurations can be specifically chosen based on the discussion herein to achieve these and other desired results.

The first structured dielectric can support propagation of a surface wave along the wave propagation interface while also resisting propagation of the wave in the bulk. This can be achieved by engineering a structure that in the bulk of the structure has a photonic gap around the frequency of the surface mode in a maximally broad range of directions at least including the direction of propagation and vicinal directions. This condition prevents the surface wave from scattering into the bulk of the first structured dielectric because the gap does not allow bulk propagation at that frequency. It should be understood that the absence of propagation in the bulk does not in general rule out propagation along the surface. Surface propagation depends on a wider set of conditions to be described below. The resulting composite evanescent waveguide can have a bandgap at the desired wavelength from the first structured dielectric side.

In addition, the second dielectric can support propagation of a surface wave along the wave propagation interface while also resisting propagation of the wave in the bulk. This can be achieved in at least two different ways. In the first case, the second dielectric can be structured and can have a photonic gap around the surface wave frequency in a maximally broad range of directions at least including the direction of propagation and its vicinity. Thus, the second dielectric restricts bulk propagation in essentially the same manner as the first structured dielectric. However, the two structured dielectrics should be different in structure, material, or orientation; otherwise surface propagation will not be possible as no boundary between the materials will be felt by a surface wave. Thus, with respect to the first structured dielectric the wave is not generally index guided on the first structured dielectric side.

In a second optional approach, the second dielectric can be uniform or irregularly structured which is uniform and isotropic of the wavelength scale (e.g. nano-porous silica). Again, the refractive index of the second dielectric can be smaller than the effective index of the surface mode. In this case the surface wave is index-guided on the second dielectric side. In other words, the surface wave experiences total internal reflection off the second dielectric. Thus, the momentum and energy conservation prevents the surface mode from scattering into the bulk of the second dielectric. These conditions necessary for surface propagation are not satisfied along the interface between two uniform dielectrics.

Specific structures and materials which satisfy these parameters can be readily determined using computer modeling or experiment. Computer modeling can be used to predict whether a particular structure satisfies the criteria above, and at the same time support propagation of electromagnetic waves along the interface. The modeling algorithm can proceed along the following steps:

(1) The desired wave frequency is chosen.

(2) The wave momentum along the interface is chosen. This in general consists of two parameters, e.g. direction of propagation and magnitude (inverse of wavelength) of the vector in the plane of the interface.

(3) A general solution of Maxwell's equations inside the first structured dielectric is found. In general, the solution comprises a finite number (including zero) of propagation modes and an infinite number of evanescent modes, which is in practice limited to a large number of evanescent modes.

(4) If the number of propagating modes is non-zero, the first dielectric is capable of propagating the mode in the bulk, which violates a general condition of the existence of the surface mode. Therefore this case is discarded, a new set of parameters (new interface momentum and/or new frequency and/or new structure) is chosen, and steps 3, 4 are repeated until the conditions are found under which there are no propagating modes in the bulk of the first structured dielectric.

(5) A general solution of Maxwell's equations inside the second dielectric (structured or not) is found. As for the first structured dielectric, the solution comprises a finite number (including zero) of propagation modes and an infinite number of evanescent modes, which is in practice limited to a large number of evanescent modes. Again, if the number of propagating modes is non-zero, this set of parameters is discarded.

(6) Once the conditions of no propagation modes on either side of the interface are identified, the two general solutions are checked against satisfying the boundary conditions at the interface. The boundary conditions are from the continuity of certain components of the electric and magnetic fields and are well known in the art of basic physics and optics.

(7) If the general solutions are not consistent with the boundary conditions, this set of parameters is discarded.

(8) If the general solutions are consistent with the boundary conditions, this implies that a surface wave exists for chosen structure and frequency and can propagate along the interface in the direction of the chosen interface momentum.

(9) Steps 1-8 are repeated until all surface waves are found for the chosen structures of the first and second dielectrics.

The above candidate structured dielectric materials can be analyzed by slicing the structured dielectric at different angles to vary the photonic band gap and effective index of refraction. The resulting materials which satisfy the above criteria can be formed into a composite evanescent waveguide in accordance with the present invention. It should be noted that the above approach can be modified as would be apparent to one skilled in the art after considering the present disclosure. For example, one can determine which frequency of propagating surface waves are desired, and materials can be found for propagating these surface waves in accordance with embodiments of the present invention. Alternatively, the materials can be chosen and a frequency, if any are allowed, satisfying the criteria discussed herein can be found.

In order to allow for propagation over a useful distance, the first dielectric structured layer can be at least substantially non-absorbing at the frequency of the surface wave. Thus, the first dielectric layer can be light transmissive at the desired frequency sufficient to prevent absorption of energy and losses as the wave propagates along the interface. Without being bound to a particular theory, the all-evanescent surface waves produced in the present invention are less lossy because confinement is based on interference, e.g. dielectric mirror, rather than electron response in a metal layer, e.g. a metallic mirror. Thus, plasmons are substantially not involved, but rather the present invention operates using purely light waves. In this way, substantially no electric current is induced during operation of the present invention such that losses resulting from Joule heating and other effects are substantially avoided.

In addition, the conditions and physical geometry of the wave propagation interface can affect the surface waves and quality of the device performance. Specifically, a rough interface can introduce unacceptable losses. Thus, it is often desirable to form the wave propagation interface having ultra smooth surface. Typically a surface roughness from about 1 nm to about 5 nm is desirable, and from about 5 nm to about 20 nm is usually acceptable.

Based on the above discussion, a composite evanescent waveguide can be produced which can propagate surface waves at a specific frequency or specific wavelength. A wide variety of wavelengths can be achieved. For example, a wavelength of about 1.55 μm, e.g. from about 1.50 μm to about 1.60 μm, can be useful for communications applications. Further, silicon is transparent to electromagnetic waves at 1.55 μm. Additionally, a wavelength in the visible range between about 0.38 μm and 0.78 μm can also be desirable.

In accordance with the principles of the present invention, the waveguide can consist essentially of the first and second dielectric layers. More specifically, waveguides of the present invention do not require a low-index substrate as in conventional photonic crystal waveguides. This allows for decreased manufacturing costs and increased range of materials which can be used. Further, the composite evanescent waveguides of the present invention can readily be formed as single mode waveguides without the use of an underlying low-index substrate. Essentially the underlying substrate, if any, does not require any special composition other than not interfering with the propagating wave.

In an additional optional embodiment of the present invention, the waveguide can further include a coupling for external coupling of waves. Coupling can be used to excite a surface wave, amplify a surface wave, imbed information such as in the form of amplitude variation or phase variations, or the like. Referring now to FIG. 3, an external coupling region 36 can be associated with a first structured layer 26a. In the external coupling region, the first structured dielectric layer can be sufficiently thin to allow a portion of the evanescent wave 22 to approach the external coupling region. An exciting beam 38 can be directed toward the structured layer. A portion of the exciting beam penetrates the structured dielectric with an intensity which decays exponentially. The decaying portion can overlap with a portion of the evanescent wave in an overlap region 40. Energy is thus transferred to the surface mode when the two waves are in resonance in a similar manner to phase matching. The surface mode of the evanescent wave can either have no energy prior to coupling or may be amplified during coupling. Typically, the second dielectric material 28a can be a uniform dielectric such as air or other gaseous mixtures, water or other liquid mixtures, in order to allow the target material to be placed on the interface.

Various external couplings can include, but are not limited to, prism coupling, evanescent coupling, butt-coupling, and the like. However, in many applications of the present invention no external coupling is required. For example, a photonic source may be integrated into the waveguide such as in on-chip communications where an LED, a laser, or another solid state light source is included within or adjacent the composite waveguide. Although such external couplings are known, coupling under conditions of the present invention results in an excited mode which occurs substantially from excitation of light modes rather than superposition of a light wave and electronic wave as in the case of surface plasmon resonance.

The composite evanescent waveguides of the present invention can be used in a variety of environments. For example, the waveguides can be used in on-chip optical communications, chemical-optical sensing, biological-optical sensing, analysis of the physical and chemical surface properties, and the like. A surface wave can be introduced along the wave propagation interface using any known device. For example, a piezoelectric transducer can be operatively connected to the composite evanescent waveguide. Although the device will typically initially produce a conventional wave form, the configuration of the present invention ensures that the propagated surface mode is all-evanescent and index guided. Other suitable wave sources can include lasers, light emitting diodes (LEDs), and the like.

Figure 5:
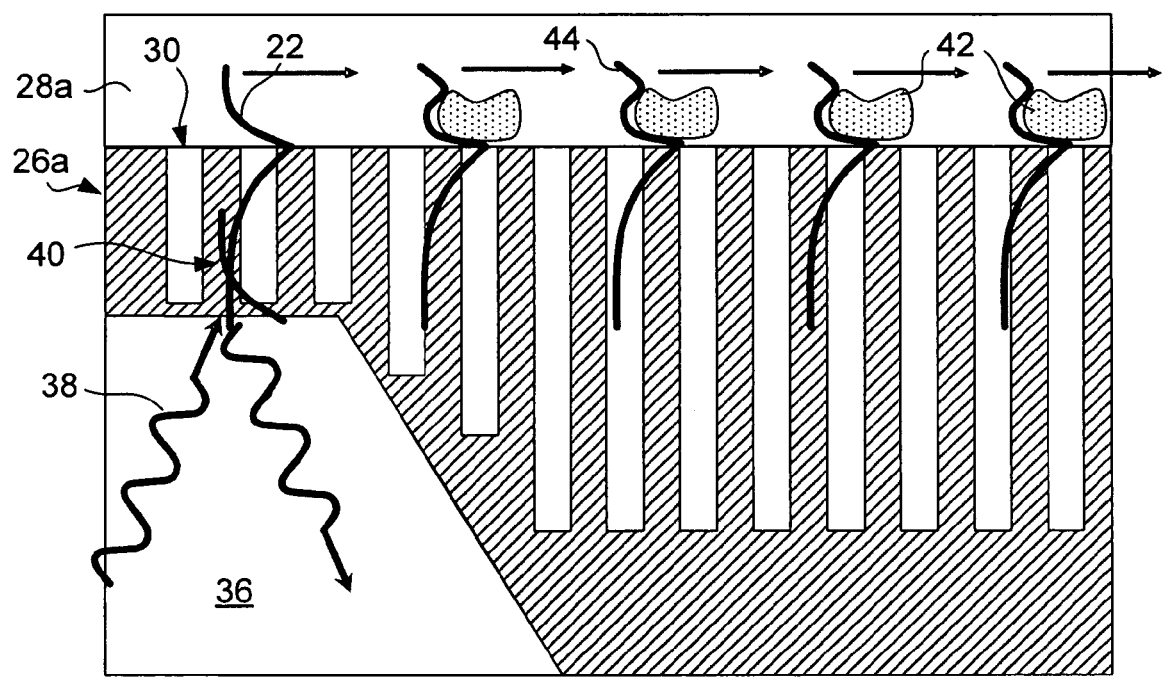
FIG. 5 illustrates a side cross-sectional view of an evanescent chemical optical sensor in accordance with yet another embodiment of the present invention.

In yet another alternative embodiment of the present invention, the composite evanescent waveguide can be incorporated into a chemical-optical sensor. FIG. 5 illustrates a chemical-optical sensor in accordance with one embodiment of the present invention. A target material 42 can be placed in contact with the wave propagation interface 30 between the first structured dielectric layer 26a and the second dielectric material 28a. If a monolayer of analyte is adsorbed on the surface at the interface, the frequency of the surface wave 22 or the reflection coefficient of the surface wave can change to form an altered surface wave 44. By detecting the altered surface wave, the change can be correlated to either a type or amount of material and can be used to estimate either qualitatively or quantitatively the presence of a particular substance. More specifically, the property change can be detected by a suitable detector operatively associated with the wave propagation interface at a point subsequent to the target material along a wave propagation path of the propagating surface light wave. The presence of the target material can change the amplitude, wave form, and/or frequency of the surface wave. The detected change can then be correlated with a known reference material. Depending on the type of sensor, the change can be correlated to a specific type of material or merely to detect the presence of a material. Such sensors can be useful in detecting hazardous biomaterials, illegal drugs, DNA hybridization events, or any other chemical species which can be selectively bound or associated with the propagation interface. Typically, the second dielectric material can be a uniform dielectric such as air or other gaseous mixtures, water or other liquid mixtures, in order to allow the target material to be placed on the interface. Further, the wave propagation interface can include a target material surface over a portion of the interface which can selectively adsorb a desired target material. Although the specific selectively adsorbent material can vary, typical materials can include, but are not limited to, selectively adsorbing polymers or other materials which can reversibly adsorb material on the surface. Alternatively, the wave propagation interface can be formed of a material which does not selectively adsorb material, in which case a target material can be directly applied to the interface. An optional coupling region 36 utilizing an exciting beam 38 to form an overlap portion 40 of the respective wave forms as previously discussed can also be used in connection with such chemical-optical sensor devices.

The composite evanescent waveguides, according to some embodiments, can be fabricated using a number of processes. Each of the constituent layers and materials discussed above can be formed via vapor deposition such as chemical vapor deposition or physical vapor deposition, deposition and subtractive lithography, electron-beam evaporation, electroless deposition, electroplating, solution phase deposition such as roll coating, spray coating, dip coating, extrusion coating, and spin casting, ink-jet printing, screen printing, solid freeform fabrication (SFF) such as stereolithography, embossing, imprint lithography, selective laser sintering, fused deposition modeling, 3D printing, and 3D ink-jet wax printing, combinations of these processes, or the like. Further, conventional thin film processes such as plasma etching, molecular beam epitaxy (MBE), MOCVD, atomic layer deposition, rapid thermal processing and other vapor deposition processes can be used. Those skilled in the art will recognize suitable manufacturing techniques which are commercially viable for a particular device configuration.

It is to be understood that the above-referenced arrangements are illustrative of the application for the principles of the present invention. Thus, while embodiments of the present invention has been described above, it will be apparent to those of ordinary skill in the art that numerous modifications and alternative arrangements can be made without departing from the principles and concepts of the invention as set forth in the claims.

What is claimed is:

1. A composite evanescent waveguide, comprising a first structured dielectric layer having a first effective dielectric constant and a second dielectric material oriented adjacent one another to form a wave propagation interface between the first structured dielectric layer and second dielectric material, said wave propagation interface capable of propagating an all-evanescent surface wave at a frequency.

2. The waveguide of claim 1, wherein the first structured dielectric layer comprises a material selected from the group consisting of silicon, glass, sapphire, diamond, quartz, silicon oxide, germanium oxide, tantalum oxide, magnesium fluoride, titanium oxide, transparent polymers, and combinations or composites thereof.

3. The waveguide of claim 2, wherein the first structured dielectric layer comprises silicon and free space in the form of cylindrical holes.

4. The waveguide of claim 1, wherein the second dielectric material is a uniform dielectric.

5. The waveguide of claim 4, wherein the uniform dielectric is air.

6. The waveguide of claim 1, wherein the second dielectric material is a structured dielectric.

7. The waveguide of claim 1, wherein at least one of the first structured dielectric layer and second dielectric material is a two-dimensional or three-dimensional periodic structured dielectric.

8. The waveguide of claim 1, wherein the wavelength is about 1.55 µm.

9. The waveguide of claim 1, wherein the wavelength is in the visible range from about 0.38 μm and 0.78 μm.

10. The waveguide of claim 1, wherein the first dielectric structured layer is at least substantially non-absorbing at the frequency.

11. The waveguide claim 1, wherein the waveguide consists essentially of the first structured dielectric layer and the second dielectric material.

12. The waveguide of claim 1, further comprising a coupling for external coupling of waves.

13. The waveguide of claim 1, further comprising a target material surface on the wave propagation interface for adsorbing a target material, wherein the second dielectric material is a uniform dielectric, and a detector is operatively associated with the wave propagation interface subsequent to the target material surface along a wave propagation direction.

14. The waveguide of claim 13, wherein the target material surface is a selectively adsorbing material which selectively adsorbs the target material.

15. A method of propagating evanescent waves comprising the step of introducing a surface wave along a wave propagation interface between a first structured dielectric layer and a second dielectric material such that the surface wave is index guided and all-evanescent.

16. The method of claim 15, wherein the second dielectric material is also a structured dielectric.

17. The method of claim 15, wherein the second dielectric material is a uniform dielectric.

18. The method of claim 15, wherein at least one of the first structured dielectric layer and second dielectric material is a two-dimensional periodic structured dielectric.

19. The method of claim 15, wherein at least one of the first structured dielectric layer and second dielectric material is a three-dimensional periodic structured dielectric.

20. The method of claim 15, further comprising the steps of:
    a) placing a target material in contact with the wave propagation interface;
    b) detecting a property change in the surface wave due to the presence of the target material; and
    c) correlating the property change with a known reference material.

21. The method of claim 15, further comprising the step of coupling a second wave with the surface wave to form a modified evanescent surface wave.

22. A method of forming a composite evanescent waveguide, comprising:
    a) forming a first structured dielectric layer having a first effective dielectric constant; and
    b) forming a second dielectric material oriented adjacent the first structured dielectric layer to form a wave propagation interface between the first structured dielectric layer and second dielectric material, said wave propagation interface capable of propagating an all-evanescent surface wave at a frequency.

23. The method of claim 22, wherein the second dielectric material is a uniform dielectric.

24. The method of claim 22, wherein the second dielectric material is a structured dielectric.

25. The method of claim 22, wherein at least one of the first structured dielectric layer and second dielectric material is a two-dimensional or three-dimensional periodic structured dielectric.

26. The method of claim 22, wherein at least one of the first structured dielectric layer and the second dielectric material are formed using a vapor deposition process.

27. The waveguide of claim 1, wherein the all-evanescent wave is index guided and experiences total internal reflection along the wave propagation interface.

* * * * *

UNITED STATES PATENT AND TRADEMARK OFFICE
CERTIFICATE OF CORRECTION

PATENT NO. : 7,406,222 B2 Page 1 of 1
APPLICATION NO. : 11/357587
DATED : July 29, 2008
INVENTOR(S) : Pavel Kornilovich It is certified that error appears in the above-identified patent and that said Letters Patent is hereby corrected as shown below:

In column 11, line 6, in Claim 11, after "waveguide" insert -- of --. (First occurrence)

Signed and Sealed this

Twenty-fifth Day of November, 2008

JON W. DUDAS
*Director of the United States Patent and Trademark Office*